United States Patent [19]

Heiba et al.

[11] 4,177,192
[45] Dec. 4, 1979

[54] SUCCINIMIDES OF AMINO AROMATIC SULFONIC ACID SALTS

[75] Inventors: El-Ahmadi I. Heiba, Princeton; Robert E. Kinney, Lawrenceville; George E. Stead, South Plainfield, all of N.J.

[73] Assignee: Mobil Oil Corporation, New York, N.Y.

[21] Appl. No.: 790,096

[22] Filed: Apr. 22, 1977

Related U.S. Application Data

[62] Division of Ser. No. 634,812, Nov. 24, 1975, Pat. No. 4,053,425, which is a division of Ser. No. 391,178, Aug. 24, 1973, abandoned.

[51] Int. Cl.$^2$ .................. C07D 403/12; C07D 207/40
[52] U.S. Cl. .................... 260/326.22; 260/326.26; 260/326.5 SF; 260/326.5 A; 260/326.5 FM; 252/33
[58] Field of Search .............. 260/326.22, 326.26, 260/326.5 A, 326.5 SF, 326.5 S, 326.5 FM; 252/33, 51.5 A

[56] References Cited

U.S. PATENT DOCUMENTS

| | | | |
|---|---|---|---|
| 2,412,557 | 12/1946 | Blair, Jr. | 252/51.5 A |
| 2,412,708 | 12/1946 | Blair, Jr. | 252/51.5 A |
| 2,490,744 | 12/1949 | Trigg | 252/51.5 A |
| 2,616,904 | 11/1952 | Asseff et al. | 252/33 |
| 3,135,765 | 6/1964 | Andress, Jr. et al. | 252/51.5 A |
| 3,401,117 | 9/1968 | Schiff | 252/33 |
| 3,431,204 | 3/1969 | Grammaria | 252/51.5 A |
| 3,789,056 | 1/1974 | Pferrmann | 260/326.5 SF |
| 3,926,820 | 12/1975 | Dickert, Jr. et al. | 252/33 |
| 3,932,288 | 1/1976 | Hoke | 252/33 |
| 4,049,565 | 9/1977 | Nnadi et al. | 252/33 |
| 4,124,512 | 11/1978 | Stournas et al. | 260/326.5 SF |

FOREIGN PATENT DOCUMENTS

| | | | |
|---|---|---|---|
| 1181366 | 2/1970 | United Kingdom | 260/326.5 SF |
| 1194286 | 6/1970 | United Kingdom | 252/33 |

*Primary Examiner*—Glennon H. Hollrah
*Assistant Examiner*—Mary Lee
*Attorney, Agent, or Firm*—Charles A. Huggett; Raymond W. Barclay; Claude E. Setliff

[57] ABSTRACT

Succinimides of aminoaryl sulfonic acid salts provide exceptional detergency, viscosity control and anticorrosion properties to lubricants and greases and to other fluid compositions useful in hydraulic systems. Ammonium, alkylammonium, alkali metal, alkaline earth metal and groups IB, IIB, VIB, VIIB, VIII metal salts of aminoaryl sulfonic acid salts, and the salts of sulfanilic acid in particular, can be reacted with alkenyl or alkylsuccinic anhydride, acid or ester, in which the alkenyl or alkyl group may contain from 8 to about 500 carbon atoms, to yield the products of this invention. These products are understood to be novel. Suitable modifications of the aforementioned are the succinimides of di(aminoaryl sulfonic acid) salts, aniline disulfonic acid salts and corresponding aminonaphthalene sulfonate salts which are also useful in the compositions of this invention.

7 Claims, No Drawings

SUCCINIMIDES OF AMINO AROMATIC SULFONIC ACID SALTS

CROSS-REFERENCE TO RELATED APPLICATIONS

This application is a division of Ser. No. 634,812, filed Nov. 24, 1975, now U.S. Pat. No. 4,053,425, which is a divisional of application Ser. No. 391,178, filed Aug. 24, 1973, now abandoned.

BACKGROUND OF THE INVENTION

1. Field of the Invention

This invention relates to succinimides of aminoaryl sulfonic acid metal or ammonium salts. In particular, this invention relates to succinimides of these salts in lubricant compositions.

2. Description of the Prior Art

In U.S. Pat. No. 3,578,422 there are disclosed fuel compositions consisting of a reaction product of hydrocarbyl succinic anhydride and alkylene polyamine, a polyether and a sulfonate. In U.S. Pat. No. 3,219,666 are disclosed compounds produced by reacting a hydrocarbyl succinic compound with an aromatic amine, such as aniline. U.S. Pat. Nos. 3,306,852 and 3,458,530 disclose phenylene diamines reacted with alkenylsuccinic anhydride. U.S. Pat. Nos. 2,987,477 and 3,634,241 disclose sulfonate salts of amides and succinimides. None of these references discloses the invention set forth in this disclosure.

SUMMARY OF THE INVENTION

It has now been discovered that hydrocarbyl succinimides of aminoaryl sulfonic acid salts are effective multifunctional additives for lubricating oils and other organic fluids used for hydraulic purposes. The basic structure to these products are believed to be as follows:

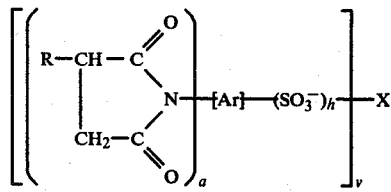

wherein R is hydrocarbyl or substituted hydrocarbyl; X is metal or $HNR'_3$ and R' is hydrogen or organo or both; a is an integer of 1 or 2 and h is an integer up to 4; Ar is any aromatic-nucleus containing radical; and v is from 1 up to the valence of X.

DESCRIPTION OF SPECIFIC EMBODIMENTS

In accordance with this invention, succinimide derivatives of ammonium or metal salts of amino-aryl sulfonic acid are prepared by reacting alkenylsuccinic acid anhydride or ester with the said metal or ammonium salt.

The preparation of the alkenylsuccinic compound is generally known (U.S. Pat. Nos. 2,568,876 and 3,219,666). Essentially, this preparation involves the reaction between 1-olefin and maleic anhydride or with halosuccinic acid or anhydride or ester. The resulting product produces by addition the corresponding alkenylsuccinic compound. The alkenyl group may contain from 5 to 1000 carbon atoms and preferably from 30 to 500, for use in lubricants or other hydraulic fluids. The olefins used for preparing the alkenylsuccinic reactant in this invention include octene-1, decene-1, dodecene-1, tetradecene-1, eicosene-1, docosene-1, and the like, as well as the branched isomers thereof, and also the dimers, trimers, and higher polymers of olefins comprising with propylene, including polypropylene, polybutene, polyisobutylene, polyamylene, and the dimers, trimers, tetramers and higher polymers of hexene, octene, decene, dodecene, tetradecene, etc. The alkenyl group may be hydrogenated to the alkyl to produce alkylsuccinic anhydrides also useful in this invention.

The aminoaryl sulfonic acid salts which are reacted with the hydrocarbyl succinic compound have the following formula:

in which X is ammonium, organoammonium, or a metal of Groups I, II, VI, VII, or VIII of the Periodic Table; a is an integer of 1 or 2, h is an integer of 1, 2, 3 or 4 and v is ordinarily the valence of X, and Ar is an aromatic group. Ar may be phenyl, naphthalene, diphenyl, dinapthalene, phenylene naphthalene, anthracene radicals, aromatic rings bridged by methylene, methylethylene, 2,2-dimethyl-propylene, oxygen, and sulfur, and these said aromatic radicals containing other substituents such as halo, hydroxy, and alkyl groups of from 1 to about 20 carbon atoms. In the case wherein Ar contains more than one nucleus the sulfonate and amino groups may be on the same ring or different rings. Preferably, a is 1 and h is 1 or 2 and X is an alkali metal or alkaline earth metal or a metal of group IIB or ammonium, $HNR'_3$ wherein R' is alkyl or aminoalkyl or poly(aminoalkyl) of from 1 to 20 carbon atoms or hydrogen or both. Of the metals, sodium, lithium, potassium, calcium, magnesium, barium, strontium and zinc are the preferred. For the purpose of this invention all variations of the aminoaryl sulfonic acid salts, regardless of the number or position of groups on the nucleus or nuclei, may also be referred to hereinafter as "sulfanilates."

The salts of this invention may range from simple monomolecular structures to complicated high molecular weight gel structures. If the aminoaryl sulfonic acid reactant contains one or more of each amino, sulfonic, or hydroxy group on the ring or rings, but the metal is monovalent, the product is a monomolecular or limited molecular weight salt. However, if the metal is polyvalent, (1) with a single amino group and sulfo group, the product is a "v-mer", that is, the number of attached aminoaryl sulfonic acid groups is the valence of the metal; (2) with more than one amino or sulfo group, then crosslinked polymeric products could result. Mixed products are also obtainable by reacting with different types of aminoaryl sulfonic acid compounds or with metals of different valences or both, defending on the molecular weight or other characteristics desired. The illustrated structures shown hereinafter are only representative of the types of such structures which may result. (Phenyl groups shown should also represent naphthyl and anthracenyl ring groups).

One method of obtaining the salts of this invention involves reaction between the hydrocarbyl succinic acid, anhydride or ester and an ammonium sulfonate (or orthanilic acid, metanilic acid or sulfanilic acid):

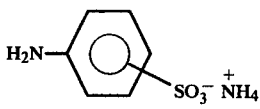

This reaction may be carried out at a temperature in the range of from about 75° C. to about 300° C. and preferably from about 90° C. to about 180° C. Usually no solvent is necessary for this reaction. However, polar or nonpolar solvents may be used whenever desired. Such solvents as hexane, dioxane, and other alkanes, aromatics, ketones, aldehydes, dimethylacetamide, dimethylformamide and the like may be used. Reaction is continued until water of condensation removed indicates imide formation.

The resulting succinimide of the ammonium sulfanilate may then be reacted, if desired, with a metal compound, replacing the ammonium group with metal. Such metal compounds as hydroxides, carbonates, bicarbonates, oxides, acetates, formates, propionates and the like may be used. A stoichiometric balance of reactants is preferred, that is, one equivalent of sulfonic group per equivalent of metal. However, excess of one reactant may be present. It should be noted that the ammonium salts themselves have useful detergent properties in lubricant compositions. They are also the preferred precursor in preparing the metal salts because of their availability and ease in producing an ionic aminoaryl sulfonic acid salt initially.

Alternatively, an ammonium sulfanilate may first be reacted with the metal reagent prior to forming the succinimide. Thus, the metal sulfanilate may be reacted with the hydrocarbyl succinic compound to yield the corresponding metal-containing succinimide. Monovalent metal products are understood to have the structure

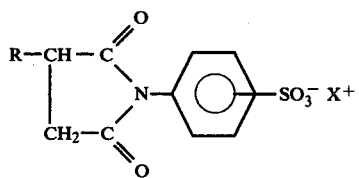

and divalent metal products

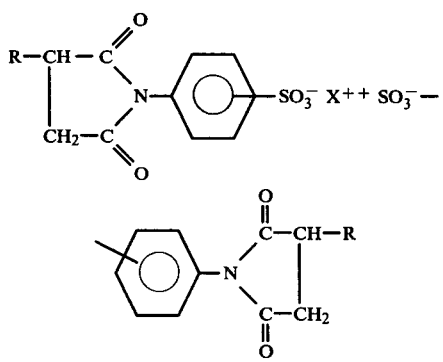

The metal sulfanilates may also be obtained by reacting the metal reagent with sulfanilic acid directly. This route is also within the scope of this invention. Reaction with the hydrocarbyl succinic compound may be carried out at the aforementioned temperatures.

A polar solvent may be used for the reaction between the metal sulfanilate and the hydrocarbyl succinic compound, e.g. ethers, alcohols, esters and amides. A preferred solvent is the N-(lower alkyl)amides, such as dimethylformamide and dimethylacetamide.

The aminoaryl sulfonic acid salt reactants of this invention are a species of a genus consisting of one or more aromatic rings, amino groups and sulfonic acid groups. By the use of such structural modifications, higher molecular weight, or polymeric, succinimides are available which may provide enhanced viscosity controls for industrial fluids.

When Ar of the previously shown structure contains a second aminoarylsulfo moiety, the final succinimide structure may be

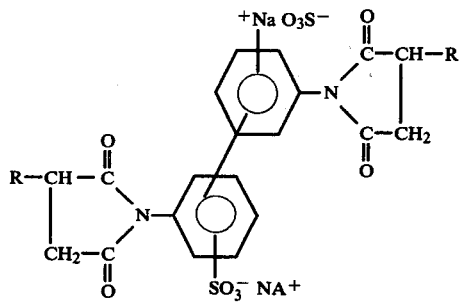

using sodium as the metal for illustration purposes. In carrying out this reaction, the disulfanilic salt may be reacted with the alkenylsuccinic compound at a 1:2 mole ratio. In the case of X being ammonium or monovalent metals, the above structure is understood to result.

If a divalent metal is used, then at least four succinimido-sulfanilate groups may be present in the molecule. Considering that the R group may contain up to 1000 carbon atoms, products of this invention may have molecular weights of over 100,000. It is speculated that polymeric structures of such products may be as follows (HSI representing the hydrocarbyl succinimido moiety) using magnesium as a typical metal:

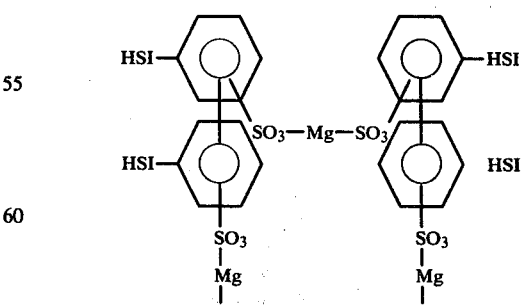

the dangling valences being attached to further sulfonic acid groups. A suggested generic formula for the repeating section of this polymer could be

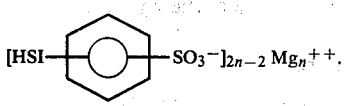

The reaction between amino di(aryl sulfonic) salts and the hydrocarbyl succinic compound are carried out at the same temperatures as previous reactions; longer reaction periods may, of course, be required. Excess reactants may be present outside the stoichiometric ratio.

A further modification of this invention is the reaction involving aminoaryl polysulfonic acid salts, especially the disulfonic salt. Again, simple compounds would be obtained with monovalent metals and ammonium; polymers may result with polyvalent metals. Two structures may be shown to represent these forms

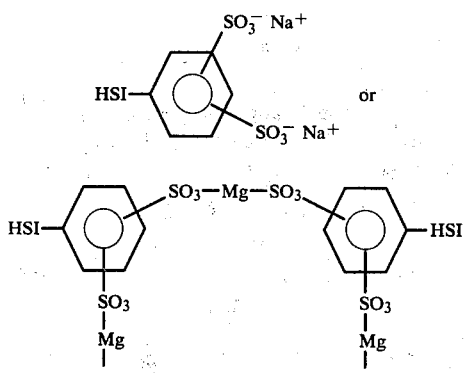

the dangling valences attached to magnesium being further linked to additional sulfonic acid groups. All such monomeric and polymeric forms are within the scope of this invention.

These additives are excellent multifunctional agents in lubricants, both liquid and grease, power transmission and heat-exchange fluids and the like media. Additive properties of these agents of particular interest are the dispersant and viscosity properties. These additives are also useful in preventing suspensoids in fluid from settling on machine or engine surfaces thereby interfering with the operation involved. They have also been shown to possess antioxidant properties as well.

Extraordinarily, oils containing certain of these additives evidence unusual film-forming characteristics under high shear. While, commercial viscosity index improvers often cannot sustain the high initial VI (which they are employed to provide) under shear, the additives of this invention permit the oil to retain initial VI to an unexpectedly greater extent. Moreover, the film thickness of the oil compositions of this invention actually increases under temporary high shear forces in certain instances, while normally a film is thinner or even disrupted. Such properties make this family of additives unique.

The additives may be used with the other well-known additives common for industrial use, such as other detergent-dispersants, VI improvers, antioxidants, anti-rust agents and the like. Such compounds as the ashless succinimides of amines and amine-metal complexes, phosphorodithioates, phenates, neutral and overbased sulfonates and the like may be present in the fluid compositions of this invention.

The following examples will serve to illustrate the gist of this invention:

EXAMPLE 1

Into a 2000 ml flask equipped with a thermometer, stirrer, gas inlet tube and condenser was added 140 grams (0.51 mole) of triethylammonium sulfanilate (prepared from triethyl amine and sulfanilic acid) and 1000 grams (0.51 mole) of polybutenyl-succinic anhydride, (diluted with 29% unreacted polybutene), the polybutenyl group being obtained by reacting maleic anhydride and polybutene of 1300 molecular weight. The reaction mixture was heated under a nitrogen atmosphere at 165° C. for 2 hours. Approximately 9 grams of water was removed. The yield of product remaining, 1130 grams, is 100% of theoretical based on the following structure:

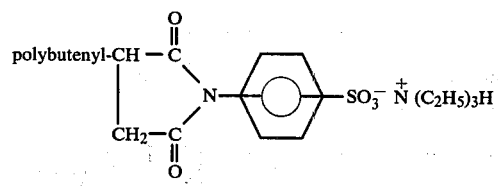

EXAMPLES 2 TO 5

Using the same procedure as in Example 1, the triethylammonium sulfanilate was reacted on an equimolar basis with alkenylsuccinic anhydride derived from the following olefins: (2) polybutene of 640 molecular weight, (3) normal octadecene, (4) iso-octadecene, and (5) polybutene of 1400 molecular weight. The reaction mixtures were heated at 165° C. under nitrogen for 2 hours in each case.

EXAMPLE 6

Into a 200 ml flask equipped with a thermometer, stirrer, gas inlet tube and condenser was added 96.7 grams (0.51 mole) of ammonium sulfanilate and 1000 grams (0.51 mole) of the polybutenyl-succinic anhydride (containing 29% unreacted polybutene) of Example 1. The reaction mixture was heated under nitrogen at 235° C. for 45 minutes removing 9 grams of water. The yield of remaining product, 1087 grams, is about 100% of theoritical.

EXAMPLE 7

Using the same equipment and procedure as in Example 1, 0.51 mole of trimethylammonium sulfanilate was reacted with 0.51 mole of the same polybutenyl-succinic anhydride at 165° C., except the reaction was conducted for 4 hours under nitrogen. Product yield was 1090 grams, about 100% of theory.

EXAMPLES 8 AND 9

Using the same conditions as in Example 7, n-butylammonium and iso-butylammonium sulfanilates were reacted on an equimolar basis with the polybutenyl-succinic anhydride. The product yield was 1144 grams, 100% of theory for both the normal isomer and isomer.

EXAMPLE 10

In a reactor similar to that of Example 1, the polybutenyl-succinimide of triethylammonium sulfanilate prepared in that example was reacted with magnesium carbonate. The reaction mixture containing 1100 grams (0.51 mole) of the succinimide and 21.4 grams (0.255 mole) of magnesium carbonate was heated at 165° C. for 2 hours under nitrogen. The temperature was raised to 185° C., and the nitrogen stream increased, these conditions being maintained for 2 hours. The yield of product was 1090 grams, 100% of theory based on

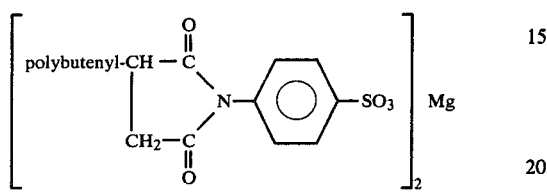

EXAMPLES 11 TO 15

The reaction of Example 10 was repeated with different metal reactants:

| Ex. | Metal Reactant | Reaction Temp. °C. | Reaction Time, hrs. | Mole Metal Per Mole |
| --- | --- | --- | --- | --- |
| 11 | NaOH | 165 | 2 | 1 |
| 12 | LiOH . H$_2$O | 165 | 2 | 1 |
| 13 | Ca(OH)$_2$ | 165 | 3 | ½ |
| 14 | ZnO | 185 | 4 | ½ |
| 15 | Ba(OH)$_2$ . 8H$_2$O | 185 | 4 | ½ |

EXAMPLE 16

Magnesium sulfanilate was prepared by reacting magnesium carbonate with sulfanilic acid in a mole ratio of 1:2 by heating to remove water and carbon dioxide.

Into a suitable reactor was added 5.5 grams (0.015 mole) of magnesium sulfanilate, 40 ml of dimethylformamide and 40 grams (0.03 mole) of the succinic anhydride of Example 1 and the mixture was heated for 5½ hours at 150° C. The product yield is 100% of theory.

EXAMPLES 17 TO 19

The succinic anhydride of Example 16 was reacted with other metal sulfanilates under the same conditions:

| Ex. | Metal | Mole Sulfanilate Per Mole Anhydride |
| --- | --- | --- |
| 17 | Calcium | ½ |
| 18 | Sodium | 1 |
| 19 | Lithium | 1 |

EXAMPLES 20 TO 23

Examples 16 to 19 were repeated except that dimethylacetamide was the solvent and the temperature was 160° C.

EXAMPLE 24

Into a reactor similar to that of Example 1 was added (0.51 mole) of the succinic anhydride and 0.25 mole (136.5 gs.) of the triethylammonium salt of disulfanilic acid. The reaction mixture was heated for 17 hours at 170° C. under a nitrogen stream. The yield of product was 1120 grams, 100% of theory based on the following structure:

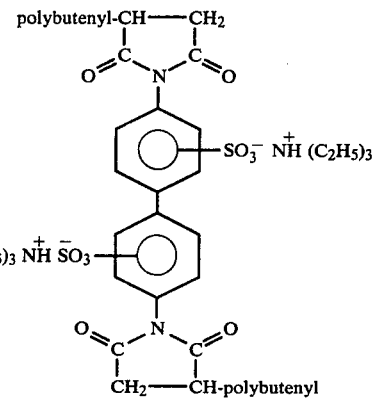

EXAMPLE 25

In a suitable reactor, 1100 grams (0.25 mole) of the product of Example 24 and 20 grams (0.5 mole) of sodium hydroxide was reacted for 3 hours at 160° C. under nitrogen to produce 475 grams of the sodium salt.

EXAMPLE 26

In a suitable reactor, 179 grams (0.5 mole) of the trimethylammonium salt of aniline disulfonic acid and 1000 grams (0.5 mole) of the polybutenyl-succinic anhydride (containing 29% unreacted polybutene) of Example 1 were reacted at 165° C. for 4 hours under nitrogen. The yield was 1159 grams, 100% of theory based on

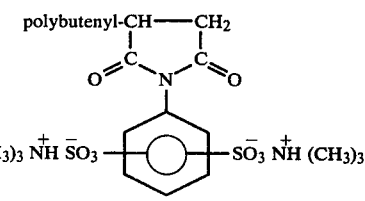

EXAMPLE 27

The trimethylammonium salt was reacted with LiOH.H$_2$O at 165° C. overnight to produce 1108 grams of the lithium salt corresponding to the ammonium salt of Example 26.

EXAMPLE 28

Into a suitable reactor were mixed 252 grams (0.5 mole) of the triethylammonium salt of 1,6-aminonaphthalene sulfonic acid and 320 grams (0.5 mole) of a polubutenyl-succinic anhydride derived from a polybutene of 640 molecular weight. The resulting product is the succinimide of 1,6-aminonaphthalene sulfonic acid triethylammonium salt.

A similar product was prepared from the 1,8-isomer salt under the same conditions.

EXAMPLE 29

The tetraethylene pentamine salt of 1,6-aminonaphthalene sulfonic acid was prepared by mixing the two reactants together in equimolar amount at a temperature of 180° C. for a period of 2 hours. The resulting ammonium salt was then reacted with the succinic anhydride of Example 28.

EXAMPLE 30

A calcium salt of 1,4,2-aminophenol sulfonic acid is reacted with the succinic anhydride of Example 1. The resulting product is the calcium salt of the alkenylsuccinimide of 1,4,2-aminophenol sulfonic acid.

EXAMPLE 31

The Mg sulfanilate of Example 16 was reacted with an alkenylsuccinic anhydride in which the alkenyl group is derived from an olefin having of molecular weight of about 157. The resulting product is the corresponding succinimide of the magnesium salt.

EXAMPLE 32

A magnesium salt was prepared by reacting the magnesium salt of disulfonic acid with the succinic anhydride of Example 1 at a mole ratio of 1:2 salt to anhydride. A similar product was obtained by reacting the product of Example 24 with magnesium carbonate.

EVALUATION OF PRODUCTS

A number of the following products, prepared in the above examples or by similar procedures, except with variations in the ammonium or metal, the alkenyl group molecular weight (R) and the type of aminoaryl sulfonic acid structure (AAS) in which "SA" is sulfanilic acid salt, "ANS" is aminonaphthalene sulfonic acid salt, "DS" is disulfanilic acid salt, "ADS" is aniline disulfonic acid salt, and "APS" is the sulfonic acid salt of 1,4,2-amino-phenol sulfonic acid salt and "NDS" is aminonaphthalene disulfonic acid salt, were evaluated.

| Salt | Ammonium or Metal | R | AAS |
|---|---|---|---|
| A | magnesium | 1300 | SA |
| B | magnesium | 1300/157 (80/20 by weight) | SA |
| C | sodium | 1400 | SA |
| D | calcium | 1300 | SA |
| E | calcium | 1300/157 (80/20) | SA |
| F | calcium | 950 | SA |
| G | calcium | 640 | SA |
| H | calcium | 251 | SA |
| I | zinc | 1300 | SA |
| J | lithium | 1300 | SA |
| K | lithium | 640 | SA |
| L | triethyl-ammonium | 1300 | SA |
| M | magnesium | 1300 | DS |
| N | lithium | 640 | DS |
| O | calcium/sodium (80/20) | 1300 | ADS |
| P | calcium | 2700 | ADS |
| Q | magnesium | 1300 | ADS |
| R | magnesium | 2700 | ADS |
| S | sodium | 1300 | ADS |
| T | triethyl-ammonium | 640 | ANS (1,6-isomer) |
| U | triethyl-ammonium | 640 | ANS (1,8-isomer) |
| V | tetraethylene-pentamine | 640 | ANS (1,6-isomer) |
| W | calcium | 1300 | APS (1,4,2-isomer) |
| X | sodium | 1300 | NDS (1,3-isomer) |

The products of this invention evidence excellent dispersant, antioxidant and viscosity index properties in such organic fluids as lubricating oils.

The following tests are used to evaluate such properties:

(1) Carbon Removal Test

In a stainless steel cylindrical cell mounted in a constant temperature bath of 100° C., one gram of nickel powder is formed in a porous bed on a 400-mesh screen. Carbon black is deposited on the screen by passing 10 ml of a dispersion of 250 ppm of carbon black in white oil through the bed at one ml per minute followed by 5 ml of white oil alone. Then the test lubricant solution (5 ml) containing 2.04% by weight of a detergent additive in a refined paraffinic white oil (Nujol) is passed through at the rate of one ml per minute. The same oil with no additive present was also tested. Light transmission measurements of the test oil are made before and after the test; the percent of light transmission is proportional to the amount of carbon present (Beer-Lambert law).

Preparation of the carbon black dispersion to prepare the bed initially involves mixing 12.5 mg of 0.18 micron diameter carbon black in 50 grams of white oil and subjecting the same to ultrasonic radiation at 80 kc/sec. for 15 minutes.

(2) Oxidation Absorption Test

This test is conducted in an oxygen circulation apparatus of the type described by Dornte (Ind. Eng. Chem., 28, pages 26–30, 1936) modified so that the rate of oxygen absorption can be recorded automatically. In general, a tube containing an oil sample (30 g) and additive is placed in a heater thermostatted at 347° F. (175° C.). After thermal equilibrium is established, the sample tube is connected with a closed oxygen circulating system. Oxygen is circulated through a fritted glass disk near the bottom of the sample tube at a rate of 5 liters per hour. The smaller the amount of oxygen absorption in a given period of time, the more stable the oil. In these examples, the time ($t_{1.0}$) required for the absorption of one mole oxygen per kilogram of oil is used to compare oils. The larger the value of $t_{1.0}$, the more stable the oil.

Sludge determinations were conducted by mixing the oxidized oil (30 grams) with 300 ml hexane, stirring overnight, and filtering through a medium frit glass filter (10 to 15 microns).

The concentration of additive in the test lubricant sample is 2.04% by weight in a solvent-refined mineral oil stock of 100 SS (at 100° F.).

(3) Viscosity Control Measurements

Oil compositions containing the products of this invention are measured for viscosity index and increase in thickening (viscosity increase per weight percent).

| RESULTS OF EVALUATION | | | | | |
|---|---|---|---|---|---|
| | Carbon | Oxidation | | Viscosity | |
| Product | Removed, % | $t_{1.0}$ hrs. | Sludge, mg. | VI | TP |
| A | 96 | 14 | 4 | 117 | (2) 1.3 |
| B | 23 | — | — | — | — |
| C | 34 | 29 | 2 | 115 | (2) 1.5 |
| D | 51 | 30.9 | 14 | 117 | (2) 1.4 |
| E | 22 | — | — | — | — |
| F | 24 | — | — | = | — — |
| G | 28 | — | — | = | — — |
| I | 21 | — | — | = | — — |
| J | 27 | 26 | 1 | 120 | (2) 1.3 |
| L | 34 | 32 | 48 | 133 | (3) 3.6 |
| M | 40 | 16 | 26 | 128 | (3) 3.5 |
| O | 36 | 22 | 7 | 299 | (3) 6.9 |
| Q | 41 | 18 | 25 | 135 | (3) 2.8 |
| R | 37 | 22 | 31 | 131.5 | (3) 3.4 |

-continued

RESULTS OF EVALUATION

| Product | Carbon Removed, % | Oxidation t$_{1.0}$ hrs. | Sludge, mg. | Viscosity VI | | TP |
|---|---|---|---|---|---|---|
| S | 12 | 21 | 1 | 160 | (3) | 3.8 |
| W | — | 28 | 14 | 161 | (3) | 5.7 |
| X | 72 | — | — | 220 | (2) | 32.0 |
| Oil | 0 | — | — | — | — | — |

*VI is viscosity index; concentration by weight in oil is in parentheses.

It is understood that the scope of this invention embraces the subject matter described herein and all obvious modifications thereof, without limitation, except as provided in the following claims.

We claim:

1. A compound of one of the formulae:

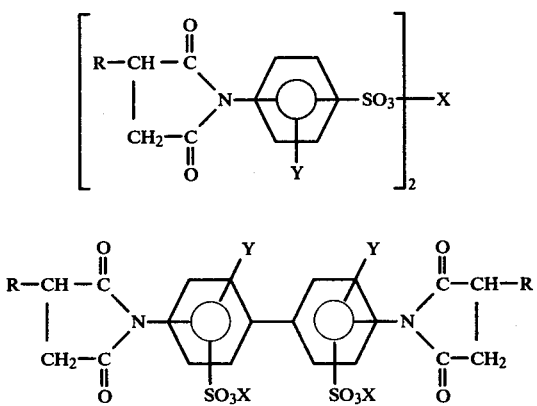

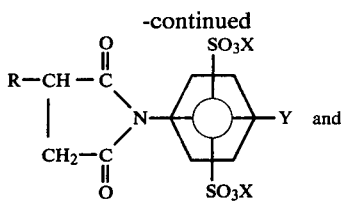

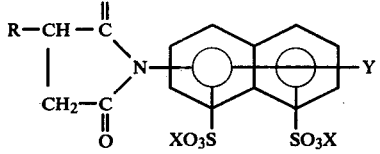

wherein X is selected from the group consisting of (1) HNR'$_3$, wherein R' is hydrogen, an alkyl group, an aminoalkyl group or a poly(aminoalkyl) group, said alkyl having from 1 to 20 carbon atoms, and (2) metal, Y is selected from the group consisting of hydrogen, halo, hydroxy and an alkyl group of from 1 to 20 carbon atoms and R is an alkenyl of from 5 to 1000 carbon atoms.

2. The compound of claim 1 wherein X is HNR'$_3$ and R' is selected from the group consisting of hydrogen, alkyl, aminoalkyl and poly(aminoalkyl), having from 1 to about 20 carbon atoms and both hydrogen and organo together.

3. The compound of claim 2 wherein R' is selected from the group consisting of hydrogen, alkyl of 1 to 5 carbon atoms and both hydrogen and said alkyl together.

4. The compound of claim 1 wherein X is a metal selected from the group consisting of alkali metal, alkaline earth metal and zinc.

5. The compound of claim 1, formula 1, wherein the metal is alkaline earth.

6. The compound of claim 1, formula 1, wherein the metal is magnesium.

7. The compound of claim 6 wherein the alkenyl has from 30 to 500 carbon atoms.

* * * * *

UNITED STATES PATENT AND TRADEMARK OFFICE
CERTIFICATE OF CORRECTION

PATENT NO. : 4,177,192

DATED : December 4, 1979

INVENTOR(S) : EL-AHMADI I. HEIBA, ROBERT E. KINNEY and GEORGE E. STEAD

It is certified that error appears in the above-identified patent and that said Letters Patent are hereby corrected as shown below:

Claim 7, line 1, change "6" to --1--.

*Signed and Sealed this*

*Nineteenth* Day of *August 1980*

[SEAL]

*Attest:*

SIDNEY A. DIAMOND

*Attesting Officer*  *Commissioner of Patents and Trademarks*